(12) United States Patent  (10) Patent No.: US 8,571,175 B2
Clemen, Jr. et al.  (45) Date of Patent: Oct. 29, 2013

(54) SYSTEM AND METHOD FOR DETERMINING IONIZATION SUSCEPTIBILITY USING X-RAYS

(75) Inventors: Mark Joseph Clemen, Jr., Bremerton, WA (US); Clarence Lavere Gordon, III, Renton, WA (US); Jerry Lee Wert, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 375 days.

(21) Appl. No.: 12/627,065

(22) Filed: Nov. 30, 2009

(65) Prior Publication Data

US 2011/0129053 A1  Jun. 2, 2011

(51) Int. Cl.
*G01B 15/00* (2006.01)
*G01N 23/00* (2006.01)
*G01D 18/00* (2006.01)

(52) U.S. Cl.
USPC ............................ 378/58; 378/207; 250/492.2

(58) Field of Classification Search
USPC ............. 378/64, 68, 69, 58, 91, 98, 204, 207, 378/210; 438/57, 953, 14, 17; 702/40; 250/492.1, 492.2
See application file for complete search history.

(56) References Cited

U.S. PATENT DOCUMENTS

| 4,816,753 | A  | * | 3/1989  | Palkuti ........................... 324/501 |
| 5,227,733 | A  | * | 7/1993  | Yamada ......................... 315/500 |
| 7,310,408 | B2 |   | 12/2007 | Filkins et al. |
| 2005/0100133 | A1 | * | 5/2005 | Reinhold ....................... 378/138 |
| 2006/0062351 | A1 | * | 3/2006 | Yokhin et al. ................... 378/86 |
| 2006/0098781 | A1 | * | 5/2006 | Bloom et al. .................. 378/119 |

OTHER PUBLICATIONS

Hignette, O. et al., "Recent Progress in Focusing X-ray Beams," http:www.ersf.eu/UsersAndScience/Publications/Highlights/2002/Methods/MET1 (6 pages).
Daneke, N. et al., "From Microfocus to Nanofocus X-Ray Inspection" (3 pages).

* cited by examiner

*Primary Examiner* — Anastasia Midkiff
(74) *Attorney, Agent, or Firm* — Thompson Hine L.L.P.

(57) ABSTRACT

A system for determining ionization susceptibility including a sample, an x-ray generator configured to generate a pulsed x-ray beam, and focusing optics disposed between the sample and the x-ray generator, the focusing optics being configured to focus the pulsed x-ray beam into a spot on the sample.

20 Claims, 2 Drawing Sheets

SYSTEM AND METHOD FOR DETERMINING IONIZATION SUSCEPTIBILITY USING X-RAYS

FIELD

The present patent application relates to the determination of ionization susceptibility and, more particularly, to the use of x-rays in the ionization and determination of ionization susceptibility and, even more particularly, to the use of pulsed, focused x-rays in the ionization and determination of ionization susceptibility of electronic devices.

BACKGROUND

Earth's magnetic field shields the planet from high energy particles, such as high energy protons and high energy ions, thereby limiting exposure to extraterrestrial high energy particles on the surface of the Earth. However, objects and persons in space lack the protection of Earth's magnetic field and, therefore, are regularly bombarded with, and potentially damaged by, high energy particles.

Active electronic devices, such as integrated circuits, may include a relatively thin metallization layer positioned over a relatively thick layer of silicon. When high energy particles pass through the silicon layer of such devices, they form ionization tracks that induce the flow of electrons that may cause damage. Depending on the design of an active electronic device, the effects of high energy particles may range from minor electrical interference to catastrophic failure. Active electronic devices deployed in space vehicles are particularly susceptible to high energy particles.

Thus, prior to deploying active electronic devices in space and other harsh environments, it is common to determine the susceptibility of such devices to damage from high energy particles using particle accelerators. Unfortunately, there are only a limited number of particle accelerators available to the public and, therefore, access is limited and access time is expensive. Furthermore, it is time-consuming and expensive to change the beam configuration of a particle accelerator, thereby further increasing costs and limiting the number of experiments that can reasonably be performed in a given period of time.

Accordingly, those skilled in the art continue to seek alternatives to particle accelerators for determining ionization susceptibility of electronic devices.

SUMMARY

In one aspect, the disclosed system for determining ionization susceptibility may include a sample (e.g., static random-access memories, microprocessors, etc.), an x-ray generator configured to generate a pulsed x-ray beam, and focusing optics disposed between the sample and the x-ray generator, the focusing optics being configured to focus the pulsed x-ray beam into a spot on the sample.

In another aspect, the disclosed system for determining ionization susceptibility may include an articulateable surface, an active electronic device mounted on the articulateable surface, an x-ray generator configured to generate a pulsed x-ray beam, wherein each pulse of the x-ray beam has a pulse width of at most about 1 nanosecond, focusing optics configured to focus the x-ray beam into a spot on the active electronic device, and a collimator disposed between the focusing optics and the active electronic device, the collimator defining an aperture therein, wherein the aperture is aligned with the spot and has a diameter of at most about 1 micron.

In yet another aspect, the disclosed method for determining ionization susceptibility of an active electronic device may include the steps of (1) generating a pulsed x-ray beam, (2) focusing the pulsed x-ray beam into a spot on the active electronic device, and (3) observing a response of the active electronic device to the focused, pulsed x-ray beam.

Other aspects of the disclosed x-ray-based system and method will become apparent from the following description, the accompanying drawings and the appended claims.

DETAILED DESCRIPTION

Figure 1:
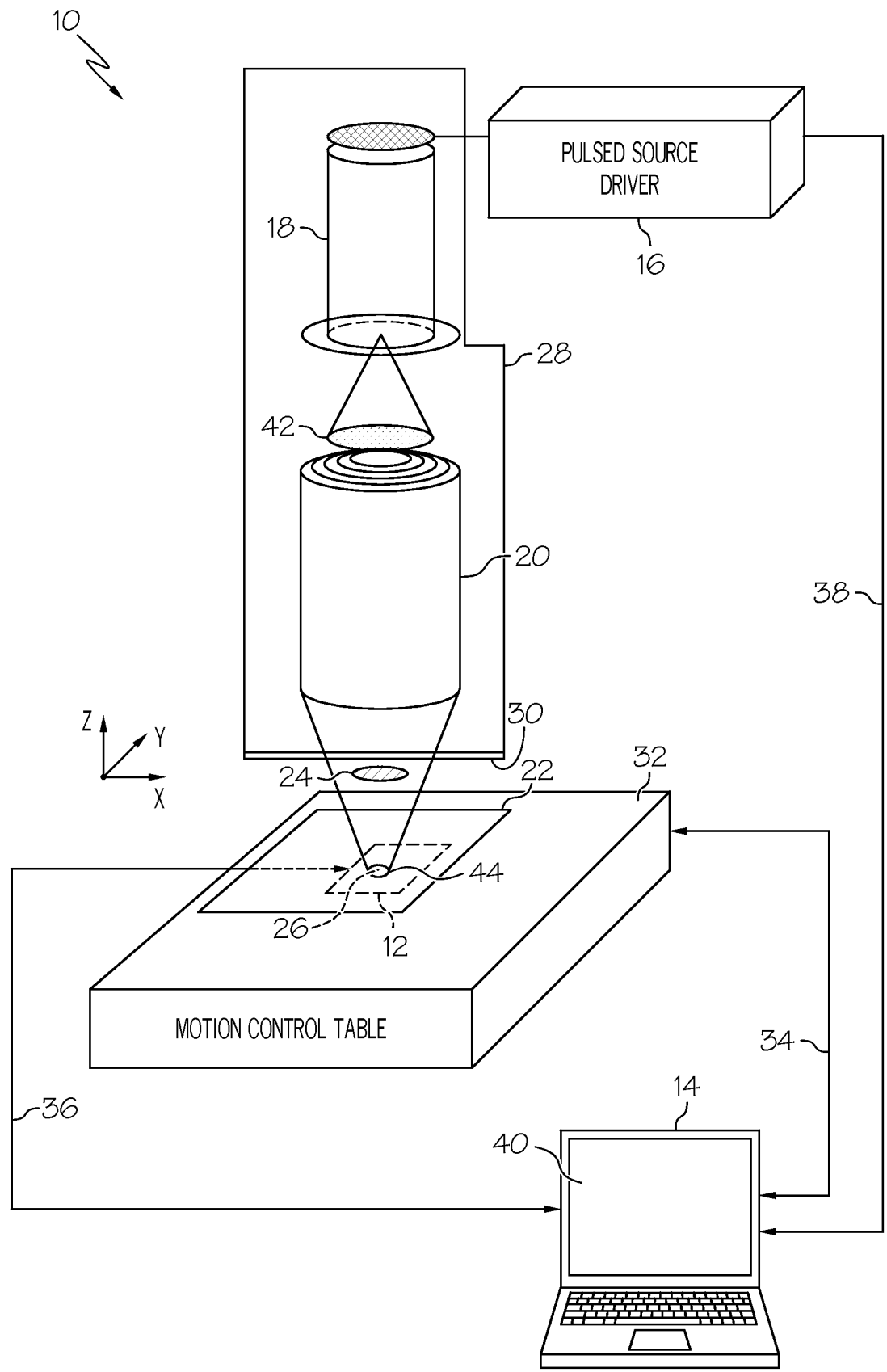
FIG. 1 is a schematic illustration of one aspect of the disclosed system for determining ionization susceptibility of an electronic device.

Referring to FIG. 1, one aspect of the disclosed x-ray-based system, generally designated 10, may be configured to determine the ionization susceptibility of a sample 12 without the need for generating high energy ions. The system 10 may include a controller 14, a pulsed source driver 16, an x-ray generator 18, focusing optics 20 and a collimator 22. The system 10 may generate a focused, pulsed x-ray beam 24 and may propagate the focused, pulsed x-ray beam 24 along the z-axis to a spot 26 on the sample 12. The focused, pulsed x-ray beam 24 may form an ionization track in the sample 12, thereby simulating the effect of high energy particles using x-rays.

Some or all of the components of the system 10 may be placed in a vacuum chamber 28 to encourage x-ray propagation. The vacuum chamber 28 may be provided with a thin vacuum window 30 when the sample 12 is outside the vacuum chamber 28.

Optionally, the system 10 may include a cooling sub-system to cool one or more components of the system 10, such as the x-ray generator 18, the focusing optics 20 and the collimator 22.

The sample 12 may be an electronic device, particularly an active electronic device, such as an integrated circuit, and may include a layer of silicon. However, those skilled in the art will appreciate that various apparatus and things may be evaluated or treated using the disclosed system 10.

The sample 12 may be mounted on an articulateable surface, such as a motion control table 32, that is articulateable in the x-y-z axis. Articulation of the motion control table 32 may be effected by controllable servomotors (not shown) or the like controlled by the controller 14 via communication line 34. The articulation of the motion control table 32 may be controlled to position the spot 26 generated by the disclosed system 10 at various desired locations on the sample 12.

The controller 14 may be any device or system, such as a processor or a computer system, configured to operate the disclosed system 10. For example, the controller 14 may be a desktop or laptop computer configured with appropriate code, software, firmware or the like to operate the disclosed system 10. In one aspect, the controller 14 may be in communication with the sample 12 via communication line 36, the motion control table 32 via communication line 34, as discussed above, and the pulsed source driver 16 via communication line 38. The communication between the controller 14 and the various components of the system 10 may be one-way, two-way or otherwise, and hard-wired, wireless or otherwise.

The controller 14 may control (e.g., activate) the sample 12 and may acquire diagnostic data from the sample 12. The controller 14 may display a diagnostic readout on an associated display 40 (e.g., a color monitor) or may otherwise facilitate the display of a diagnostic readout. Furthermore, the controller 14 may store the acquired diagnostic data in an associated storage medium (not shown) or may otherwise facilitate the storage of the acquired diagnostic data (e.g., in an external hard drive).

The pulsed source driver 16 may be any circuit, device or system capable of supplying high precision, high voltage pulsed power to the x-ray generator 18. The controller 14 may initiate an active phase of the system 10 by activating the pulsed source driver 16. Specifically, the controller 14 may provide the pulsed source driver 16 with on/off instructions and, when in the active phase (i.e., the "on" phase), may also specify the pulse width, the pulse frequency, and the pulse magnitude (e.g., voltage) of the power to be supplied by the pulsed source drive 16, thereby dictating the resulting pulse width, pulse frequency and energy of the resulting x-rays generated by the x-ray generator 18. The pulse source driver 16 may receive synchronization signals from the control system 14 to apply the laser pulse synchronization with determined electric states (e.g., clock edges) of the test article 12.

The x-ray generator 18 may be any apparatus or system capable of generating a synchronized pulsed x-ray beam 42 that is capable of being focused into the spot 26. The pulsed x-ray beam 42 may be comprised of relatively short pulses, such as, for example, pulses less than 1 nanosecond (e.g., 10 picosecond to 100 picosecond pulses). The energy of the pulsed x-ray beam 42 may be controlled by the controller 14, and may range, for example, from about 1 keV to about 100 keV (e.g., 10 keV). A 10 keV x-ray beam is generally sufficient to propagate through a typical 300 micron silicon wafer, including the top metallization layer.

In accordance with a first aspect, the x-ray generator 18 may be an x-ray tube. In a first implementation of the first aspect, the x-ray generator 18 may be a micro-focused x-ray tube, which may have focal spot sizes less than about 10 microns. A commercially available micro-focused x-ray tube useful in the disclosed system 10 is the L8121-03 150 kV micro-focus x-ray source, available from Hamamatsu Corporation of Bridgewater, N.J. This would be appropriately fitted with a pulsed cold-cathode emitter to best generate the short pulses of x-rays. In a second implementation of the first aspect, the x-ray generator 18 may be a nano-focused x-ray tube, which may have focal spot sizes less than 1 micron. A commercially available nano-focused x-ray tube useful in the disclosed system 10 is the phoenix/x-ray xs/160hpnf, available from GE Sensing & Inspection Technologies of Wunstorf, Germany. This would be also be appropriately fitted with a pulsed cold-cathode emitter to best generate the short pulses of x-rays.

In accordance with a second aspect, the x-ray generator 18 may be an inverse Compton scattering x-ray generator. An inverse Compton scattering x-ray generator may include a fast pulse laser and an electron accelerator, including the magnetic and electric focusing optics for the electron beam. An example of a system and method for generating an x-ray pulse using inverse Compton scattering is described in U.S. Pat. No. 7,310,408.

At this point, those skilled in the art will appreciate that the ionization effects of various different high energy particles may be simulated by controlling the energy, the pulse width and/or the pulse frequency of the pulsed x-ray beam 42 emitted from the x-ray generator 18. For example, relatively high energy and/or relatively high pulse widths may be used to simulate high energy iron ions, which create relatively large ionization tracks, while relatively lower energy and/or relatively lower pulse widths may be used to simulate high energy protons, which create smaller ionization tracks than high energy iron ions.

The focusing optics 20 may be disposed between the x-ray generator 18 and the sample 12 and may focus the pulsed x-ray beam 42 into the spot 26 on the sample 12, resulting in a focused, pulsed x-ray beam 24. The focusing optics 20 may be any x-ray focusing optics capable of focusing the pulsed x-ray beam 42 into a spot 26 having a maximum width in the x-y plane of at most about 10 microns and, in one particular implementation, at most about 1 micron.

In one aspect, the focusing optics 20 may comprise an array of symmetrical cylindrical mirrors, similar to an x-ray telescope. For example, the focusing optics 20 may be constructed in a manner similar to the Wolter Type I x-ray telescope. In another aspect, the focusing optics 20 may be based on the Kirkpatrick-Baez system, wherein two orthogonal mirrors focus the incident x-ray beam successively in the horizontal and vertical planes. At this point, those skilled in the art will appreciate that any available technique capable of focusing the pulsed x-ray beam 42 into a small (e.g., 10 micron or less) spot 26 may be used without departing from the scope of the present disclosure.

The collimator 22 may be disposed between the focusing optics 20 and the sample 12, and may include an aperture 44 through which appropriately focused x-rays may pass to the sample 12 while other x-rays are rejected, thereby ensuring that the spot 26 on the sample 12 has the desired size. For example, the aperture 44 may have a diameter of about 1 micron to ensure that the spot 26 on the sample 12 is at most 1 micron wide.

Figure 2:
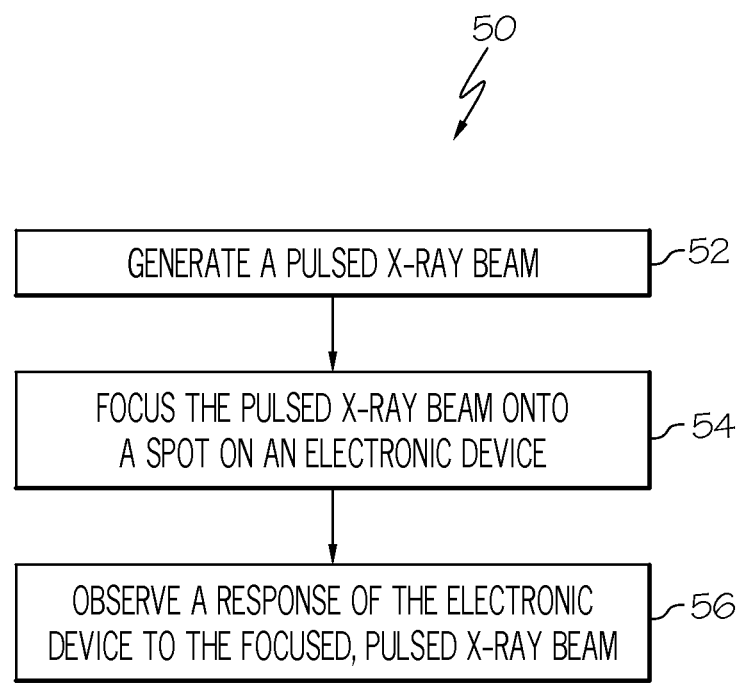
FIG. 2 is a flow chart illustrating one aspect of the disclosed method for determining the ionization susceptibility of an electronic device.

Accordingly, as shown in FIG. 2, one aspect of the disclosed method, generally designated 50, for determining the ionization susceptibility of an active electronic device 12 may begin at block 52 with the generation of a pulsed x-ray beam 42. The pulsed x-ray beam 42 may be generated in response to a command signal sent to the pulse source driver 16 by the controller 14. The command signal may specify the desired energy, pulse width and/or pulse frequency of the emitted pulsed x-ray beam 42, the selection which may depend on the type of testing being performed.

At block 54, the pulsed x-ray beam 42 may be focused into a spot 26 on the active electronic device 12. As discussed above, the focusing step may be achieved using focusing optics 20, and a final collimator 22 may ensure that the resulting spot 26 is no larger than a pre-determined size (e.g., 1 micron).

As shown in block 56, a response of the active electronic device 12 to the focused, pulsed x-ray beam 24 may be observed. For example, the controller 14 may collect data from the active electronic device 12 while it is active and being bombarded with the focused, pulsed x-ray beam 24. The collected data may be processed, displayed on the display 40 and/or stored in a storage medium, among other things.

Finally, while not shown in FIG. 2, the process may be repeated at various (or all) locations on the sample 12 and/or until significant susceptibilities are observed. For example, the controller 14 may articulate the motion control table 32 in the x-y plane to raster the spot 26 over various (or all) portions of the sample 12. All collected data may be mapped by the controller 14. This process may likewise be repeated at various times at such locations, relative to a specific clock or critical process in the device under test and/or until significant susceptibilities are observed.

Accordingly, the disclosed x-ray-based system and method allow users to form ionization tracks and observe effects that would otherwise arise from the ionization from various high energy particles (e.g., high energy protons and high energy ions) on various samples (e.g., active electronic devices) using x-rays, thereby limiting or even eliminating the need for large and expensive particle accelerators. Furthermore, the disclosed x-ray-based system 10 and method 50 allow users to control the energy, pulse width and/or pulse frequency of the x-rays to mimic various high energy particles that may be encountered in space, as well as the location of the spot (i.e., the test site) or the timing of the spot relative to a critical function or clock in the device under test.

Although various aspects of the disclosed x-ray-based system and method have been shown and described, modifications may occur to those skilled in the art upon reading the specification. The present application includes such modifications and is limited only by the scope of the claims.

What is claimed is:

1. A system comprising:
    an integrated circuit comprising a silicon layer with a metallization layer positioned over the silicon layer and wherein the metallization layer is thinner than the silicon layer;
    an x-ray generator configured to generate a pulsed x-ray beam, wherein the pulsed x-ray beam is at least about 1 keV and of sufficient energy to propagate through the silicon layer and the to metallization layer, wherein each pulse of said pulsed x-ray beam has a pulse width of at most about 1 nanosecond; and
    focusing optics disposed between said sample and said x ray generator said pulsed x-ray beam, said focusing optics being configured to focus said pulsed x-ray beam into a spot on the integrated circuit.

2. The system of claim 1 wherein said x-ray generator includes a pulsed micro-focused x-ray tube.

3. The system of claim 1 wherein said x-ray generator includes a pulsed nano-focused x-ray tube.

4. The system of claim 1 wherein said x-ray generator includes an inverse Compton scattering x-ray generator.

5. The system of claim 1 wherein each pulse of said pulsed x-ray beam has a pulse width in a range of about 10 picoseconds to about 100 picoseconds.

6. The system of claim 1 wherein said pulsed x-ray beam has an energy of at least 1 keV.

7. The system of claim 1 wherein said focused x-ray spot on the sample has a maximum width of at most about 1 micron.

8. The system of claim 1 further comprising a collimator disposed between said focusing optics and said sample, said collimator defining an aperture therein.

9. The system of claim 8 wherein said aperture has a diameter of at most about 1 micron.

10. The system of claim 1 wherein said sample is mounted on a motion control table.

11. The system of claim 1 further comprising a pulsed source driver configured to supply power to said x-ray generator.

12. The system of claim 11 further comprising a controller in communication with said pulsed source driver.

13. A system for determining ionization susceptibility comprising:
    an articulateable surface;
    an integrated circuit comprising a silicon layer with a metallization layer positioned over the silicon layer and wherein the metallization layer is thinner than the silicon layer, wherein the integrated circuit is mounted on said articulateable surface;
    an x-ray generator configured to generate a pulsed x-ray beam, of at least about 1 keV and of sufficient energy to propagate through the silicon layer and the to metallization layer, wherein each pulse of said pulsed x-ray beam has a pulse width of at most about 1 nanosecond;
    focusing optics disposed between said integrated circuit and said pulsed x-ray beam and configured to focus said pulsed x-ray beam into a spot on the integrated circuit; and
    a collimator disposed between said focusing optics and the integrated circuit, said collimator defining an aperture therein, wherein said aperture is aligned with said spot and has a diameter of at most about 1 micron.

14. A method for determining ionization susceptibility of an integrated circuit comprising a silicon layer with a metallization layer positioned over the silicon layer and wherein the metallization layer is thinner than the silicon layer comprising the steps of;
    generating a pulsed x-ray beam of at least about 1 keV and of sufficient energy to propagate through the silicon layer and the to metallization layer, wherein each pulse of said pulsed x-ray beam has a pulse width of at most about 1 nanosecond;
    focusing said pulsed x-ray beam into a spot on the integrated circuit; and
    observing a response of the integrated circuit to said focused, pulsed x-ray beam.

15. The method of claim 14 wherein said step of generating said pulsed x-ray beam includes the use of at least one of a micro-focused x-ray tube, a nano-focused x-ray tube, and an inverse Compton scattering x-ray generator.

16. The method of claim 14 wherein said spot has a maximum width of at most about 1 micron.

17. The method of claim 14 wherein said observing step includes communication between said active electronic device and a controller.

18. The system of claim 1 wherein the energy of the pulsed x-ray beam is from about 1 keV to about 100 keV.

19. The system of claim 1 wherein the energy of the pulsed x-ray beam is 10 keV.

20. The system of claim 1 wherein the energy of the pulsed x-ray beam is from about 10 keV to about 100 keV.

* * * * *

UNITED STATES PATENT AND TRADEMARK OFFICE
CERTIFICATE OF CORRECTION

PATENT NO. : 8,571,175 B2  
APPLICATION NO. : 12/627065  
DATED : October 29, 2013  
INVENTOR(S) : Mark Joseph Clemen, Jr., Clarence Lavere Gordon, III and Jerry Lee Wert Page 1 of 1

It is certified that error appears in the above-identified patent and that said Letters Patent is hereby corrected as shown below:

In the Claims

Column 5, Claim 1, Line 32 reads "silicon layer and the to metallization layer, wherein each"
It should read -- silicon layer and the top metallization layer, wherein each --

Column 6, Claim 13, Line 17 reads "propagate through the silicon layer and the to metalliza"
It should read -- propagate through the silicon layer and the top metalliza --

Column 6, Claim 14, Line 35 reads "layer and the to metallization layer, wherein each pulse"
It should read -- layer and the top metallization layer, wherein each pulse --

Signed and Sealed this
Twenty-eighth Day of January, 2014

Michelle K. Lee
*Deputy Director of the United States Patent and Trademark Office*